(12) United States Patent
Sampson (10) Patent No.: US 7,682,809 B2
(45) Date of Patent: Mar. 23, 2010

(54) DIRECT ATP RELEASE SEQUENCING

(75) Inventor: Jeffrey R. Sampson, San Francisco, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 118 days.

(21) Appl. No.: 12/013,377

(22) Filed: Jan. 11, 2008

(65) Prior Publication Data

US 2009/0181374 A1 Jul. 16, 2009

(51) Int. Cl.
C12P 19/34 (2006.01)
C12Q 1/68 (2006.01)
G01N 15/06 (2006.01)
C07H 21/04 (2006.01)

(52) U.S. Cl. .................. 435/91.1; 435/6; 536/23.1; 536/24.3; 422/68.1

(58) Field of Classification Search .............. 435/6, 435/91.1; 536/23.1, 24.3; 422/68.1
See application file for complete search history.

(56) References Cited

U.S. PATENT DOCUMENTS 6,613,523 B2 9/2003 Fischer

OTHER PUBLICATIONS

Gharizadeh, et al., "Improvements in Pyrosequencing technology by employing Sequenase polymerase," Analytical Biochemistry, 2004, 330(2):272-280.

Guranowski, et al., "Catabolism of diadenosine 5',5'''-P1,P4-tetraphosphate in procaryotes. Purification and properties of diadenosine 5',5'''-P1,P4-tetraphosphate (symmetrical) pyrophosphohydrolase from *Escherichia coli* K12," Journal of Biological Chemistry, 1983, 258(24):14784-14789.

Han et al., "One-flask synthesis of dinucleoside tetra- and pentaphosphates," Organic Letters, 2006, 8(10):2075-2077.

Nyren, P., "Enzymatic method for continuous monitoring of DNA polymerase activity," Analytical Biochemistry, 198, 167(2):35-238.

Plateau et al., "Catabolism of bis(5'-nucleosidyl) oligophosphates in *Escherichia coli*: metal requirements and substrate specificity of homogeneous diadenosine-5',5'''-P1,P4-tetraphosphate pyrophosphohydrolase," Biochemistry, 1985, 24(4):914-922.

Ronghi, et al., "Real-time DNA sequencing using detection of pyrophosphate release," Analytical Biochemistry, 1996, 242(1):84-89.

Sillero, et al., "Synthesis of dinucleoside polyphosphates catalyzed by firefly luciferase," European Journal of Biochemistry, 1991, 202(2):507-513.

*Primary Examiner*—Jezia Riley (57) ABSTRACT

A method for sequencing a nucleic acid is provided. In certain embodiments, the method includes contacting a nucleic acid duplex comprising a nucleic acid template and a primer annealed to the template with a reagent mix under primer extension conditions to produce an extended primer and ATP. The reagent mix may contain an adenosine-2'-deoxynucleoside tetraphosphate moiety and a polymerase. The method further includes detecting the produced ATP. Also provided are adenosine-2'-deoxynucleoside tetraphosphate moieties that find use in the subject methods. Also provided are kits containing the adenosine-2'-deoxynucleoside tetraphosphate moieties for use in the subject methods.

20 Claims, 2 Drawing Sheets

DIRECT ATP RELEASE SEQUENCING

BACKGROUND

In pyrosequencing, a sequencing primer is hybridized to a single stranded DNA template to form a nucleic acid duplex. The duplex is incubated with the enzymes DNA polymerase, ATP sulfurylase, and luciferase, and with the substrates adenosine 5'-phosphosulfate (APS) and luciferin. In addition, one of the four deoxynucleotide triphosphates (dNTPs; i.e., dATP, dGTP, dGTP, or TTP) is added. If the dNTP is complementary to the next position on the nucleic acid template, the deoxynucleotide is incorporated into the elongating nucleic acid strand, and a pyrophosphate (PPi) molecule is released stoichiometrically. Importantly, pyrophosphate is only released if the complementary nucleotide is incorporated into the elongating nucleic acid chain.

The release of PPi indicates that a reaction has occurred. Consequently, the identity of the nucleotide incorporated into the elongating nucleic acid strand can be determined based on whether or not PPi has been released. The pyrophosphate released in these reactions can be detected in a variety of ways, including enzymatically. First, sulfurylase quantitatively converts PPi to adenosine triphosphate (ATP) in the presence of APS. Subsequently, this ATP is consumed in a luciferin-luciferase reaction to generate PPi and detectable light in amounts that are proportional to the amount of ATP. Thus, each light signal is proportional to the number of nucleotides incorporated into the growing strand. Moreover, pyrosequencing depends upon the release of PPi to initiate the cascade of reactions resulting in the emission of a detectable light signal. Such methods allow a base to be identified at a target position. Successive iterations of the method with each dNTP allow a DNA template to be sequenced.

SUMMARY

A method for sequencing a nucleic acid is provided. In certain embodiments, the method includes contacting a nucleic acid duplex comprising a nucleic acid template and a primer annealed to the template with a reagent mix under primer extension conditions to produce an extended primer and ATP. The method further includes detecting the produced ATP. The reagent mix may contain an adenosine-2'-deoxynucleoside tetraphosphate moiety and a polymerase. Also provided are adenosine-2'-deoxynucleoside tetraphosphate moieties that find use in the subject methods. Also provided are kits containing the adenosine-2'-deoxynucleoside tetraphosphate moieties for use in the subject methods.

DEFINITIONS

The term "nucleic acid" and "polynucleotide" are used interchangeably herein to describe a polymer of any length, e.g., greater than about 10 bases, greater than about 100 bases, greater than about 500 bases, greater than 1000 bases, usually up to about 10,000 or more bases composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The terms "nucleoside", "nucleotide", "deoxynucleoside", and "deoxynucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the "nucleoside", "nucleotide", "deoxynucleoside", and "deoxynucleotide" include those moieties that contain not only conventional ribose and deoxyribose sugars, but other sugars as well. Modified nucleosides, nucleotides, deoxynucleosides or deoxynucleotides also include modifications on the sugar moiety, e.g., wherein one or more of the hydroxyl groups are replaced with halogen atoms or aliphatic groups, or are functionalized as ethers, amines, or the like.

Naturally occurring nucleotides or nucleosides are defined herein as adenine (A), thymine (T), guanine (G), cytosine (C). It is recognized that certain modifications of these nucleotides or nucleosides occur in nature. However, modifications of A, T, G, and C that occur in nature that affect hydrogen bonded base pairing are considered to be non-naturally occurring. For example, 2-aminoadenosine is found in nature, but is not a "naturally occurring" nucleotide or nucleoside as that term is used herein. Other non-limiting examples of modified nucleotides or nucleosides that occur in nature that do not affect base pairing and are considered to be naturally occurring are 5-methylcytosine, 3-methyladenine, O(6)-methylguanine, and 8-oxoguanine.

Nucleotides or nucleosides may be defined as nitrogenous nucleotides or nucleosides derived from purine or pyrimidine. "Modified nucleotides", "modified nucleosides", "nucleotide analogs", or "nucleoside analogs" (excluding A, T, G, and C) include for example, nucleotides or nucleosides having a structure derived from purine or pyrimidine (i.e., nucleotide or nucleoside analogs). For example and without limitation, a modified adenine may have a structure including a purine with a nitrogen atom covalently bonded to C6 of the purine ring as numbered by conventional nomenclature known in the art. In addition, it is recognized that modifications to the purine ring and/or the C6 nitrogen may also be included in a modified adenine. A modified thymine may have a structure comprising at least a pyrimidine, an oxygen atom covalently bonded to the C4 carbon, and a C5 methyl group. Again, it is recognized by those skilled in the art that modifications to the pyrimidine ring, the C4 oxygen and/or the C5 methyl group may also be included in a modified adenine. For example and without limitation, a modified guanine may have a structure comprising at least a purine, and an oxygen atom covalently bonded to the C6 carbon. A modified cytosine may have a structure including a pyrimidine and a nitrogen atom covalently bonded to the C4 carbon. Modifications to the purine ring and/or the C6 oxygen atom may also be included in modified guanine nucleotides or nucleosides. Modifications to the pyrimidine ring and/or the C4 nitrogen atom may also be included in modified cytosine nucleotides or nucleosides.

Some examples of modified nucleotides include, without limitation, 2'-deoxynucleotides include 2'-deoxyadenosine-monophosphate (dAMP), 2'-deoxyguanosine-monophosphate (dGMP), 2'-deoxycytidine-monophosphate (dCMP), 2'-deoxythymidine-monophosphate (thymidine) (dTMP or TMP), 2-amino-2'-deoxyadenosine-monophosphate, 2-thio-2'deoxythymidine-monophosphate (or 2-thiothymidine-monophosphate), 2-thio-2'-deoxycytidine-monophosphate, 2'-deoxyinosine-monophosphate, 2'-deoxypyrrolopyrimidine-monophosphate (dPMP).

Nucleotides useful in the invention include any nucleotide or nucleotide analog, whether naturally-occurring or synthetic. Exemplary nucleotides include phosphate esters of deoxyadenosine, deoxycytidine, deoxyguanosine, deoxythymidine, adenosine, cytidine, guanosine, and uridine. Other nucleotides include an adenine, cytosine, guanine, thymine base, a xanthine or hypoxanthine; 5-bromouracil, 2-aminopurine, deoxyinosine, or methylated cytosine, such as 5-methylcytosine, and N4-methoxydeoxycytosine. Also included are bases of polynucleotide mimetics, such as methylated nucleic acids, e.g., 2'-O-methRNA, peptide nucleic acids, modified peptide nucleic acids, locked nucleic acids and any other structural moiety that can act substantially like a nucleotide or base, for example, by exhibiting base-complementarity with one or more bases that occur in DNA or RNA and/or being capable of base-complementary incorporation, and includes chain-terminating analogs. A nucleotide corresponds to a specific nucleotide species if they share base-complementarity with respect to at least one base Analogs may also be derivatives of purines without restrictions to atoms covalently bonded to the C6 carbon. These analogs would be defined as purine derivatives. Analogs may also be derivatives of pyrimidines without restrictions to atoms covalently bonded to the C4 carbon. These analogs would be defined as pyrimidine derivatives. Purine analogs include those having the capability of forming stable base pairs with pyrimidine analogs without limitation to analogs of A, T, G, and C as defined. Purine analogs also include those not having the capability of forming stable base pairs with pyrimidine analogs without limitation to analogs of A, T, G, and C.

In addition to purines and pyrimidines, modified nucleotides or analogs, as those terms are used herein, include any compound that can form a hydrogen bond with one or more naturally occurring nucleotides or with another nucleotide analog. Any compound that forms at least two hydrogen bonds with T or with a derivative of T is considered to be an analog of A or a modified A. Similarly, any compound that forms at least two hydrogen bonds with A or with a derivative of A is considered to be an analog of T or a modified T. Similarly, any compound that forms at least two hydrogen bonds with G or with a derivative of G is considered to be an analog of C or a modified C. Similarly, any compound that forms at least two hydrogen bonds with C or with a derivative of C is considered to be an analog of G or a modified G. It is recognized that under this scheme, some compounds will be considered for example to be both A analogs and G analogs (purine analogs) or both T analogs and C analogs (pyrimidine analogs).

The term "complementary, "complement," or "complementary nucleic acid sequence" refers to the nucleic acid strand that is related to the base sequence in another nucleic acid strand by the Watson-Crick base-pairing rules. In general, two sequences are complementary when the sequence of one can hybridize to the sequence of the other in an anti-parallel sense wherein the 3'-end of each sequence hybridizes to the 5'-end of the other sequence and each A, T, G, and C of one sequence is then aligned with a T, A, C, and G, respectively, of the other sequence. Complementation of modified nucleotide analogs is defined according to the parent nucleotide. Complementation of modified nucleotides analogs does not require the ability to form stable hydrogen bonded base pairs. In other words, two modified nucleotide analogs may be complementary according to the identity of the modified nucleotide analog but may not form a stable base pair. Complementation of nucleotide analogs which are not considered derivatives of A, T, G, or C is defined according to an ability to form a stable base pair with a nucleotide or analog thereof. For example, a particular derivative of C (i.e., 2-thio-cytosine) may not form a stable base pair with G, but is still considered complementary.

The term "duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick basepairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

The terms "hybridization", and "hybridizing", in the context of nucleotide sequences are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the hybridization of the two sequences. Increased stringency can be achieved by elevating the temperature, increasing the ratio of co-solvents, lowering the salt concentration, and the like.

The terms "hybrid" and "duplex" refer to a double-stranded nucleic acid molecule formed by hydrogen bonding between complementary nucleotides.

The term "primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. A primer serves as an initiation point for nucleotide polymerization catalyzed by either DNA polymerase, RNA polymerase or reverse transcriptase.

The term "template" denotes a nucleic acid molecule that can be used by a nucleic acid polymerase to direct the synthesis of a nucleic acid molecule that is complementary to the template according to the rules of Watson-Crick base pairing. For example, DNA polymerases utilized DNA to synthesize another DNA molecule having a sequence complementary to a strand of the template DNA. RNA polymerases utilize DNA as a template to direct the synthesis of RNA having a sequence complementary to a strand of the DNA template.

DNA reverse transcriptases utilize RNA to direct the synthesis of DNA having a sequence complementary to a strand of the RNA template.

The phrase "primer extension conditions" denotes conditions that permit for polymerase mediated primer extension by addition of nucleotides to the end of the primer molecule using the template strand as a template.

If a subject primer "corresponds to" or is "for" a certain nucleic acid template, the primer base pairs with, i.e., specifically hybridizes to, that nucleic acid template. As will be discussed in greater detail below, a primer for a particular nucleic acid template and the particular nucleic acid template, or complement thereof, usually contain at least one region of contiguous nucleotides that is identical in sequence.

The term "reagent mix", as used herein, refers to a combination of reagents, that are interspersed and not in any particular order. A reagent mix is heterogeneous and not spatially separable into its different constituents. Examples of mixtures of elements include a number of different elements that are dissolved in the same aqueous solution, or a number of different elements attached to a solid support at random or in no particular order in which the different elements are not spatially distinct.

The term "sequencing" refers to determining the identity of one or more nucleotides, i.e., whether a nucleotide is a G, A, T or C.

The phrase "surface-bound enzyme" refers to an enzyme that is immobilized on a surface of a solid substrate, where the substrate can have a variety of configurations, e.g., a sheet, bead, or other structure. In certain embodiments, the enzymes employed herein are present on a surface of the same substrate.

The term "luciferase" refers to an adenosine triphosphate (ATP) hydrolase that catalyzes the hydrolysis of ATP into constituent adenosine monophosphate (AMP) and pyrophosphate (PPi) along with the release of light (hυ). A luciferase has an activity described as EC 1.13.12.7, according to IUBMB enzyme nomenclature. The systematic name for a luciferase is *Photinus*-luciferin 4-monooxygenase (ATP-hydrolyzing). The *Photinus pyralis* luciferase is a type of luciferase.

The terms "sulfurylase" or "ATP sulfurylase" refer to a transferase that catalyzes the formation of ATP from PPi in the presence of adenosine 5'-phosphosulfate (APS). A sulfurylase has an activity described as EC 2.7.7.4, according to IUBMB enzyme nomenclature. The systematic name for a sulfurylase is ATP:sulfate adenylyltransferase.

The term "apyrase" refers to a nucleotide hydrolase that catalyzes the hydrolysis of nucleoside triphosphate and nucleoside diphosphate into constituent nucleoside monophosphate and phosphate. An apyrase has an activity described as EC 3.6.1.5, according to IUBMB enzyme nomenclature. The systematic name for an apyrase is ATP diphosphohydrolase (phosphate-forming).

The term "pyrophosphohydrolase" refers to a dinucleoside tetraphosphate hydrolase that catalyzes the symmetric hydrolysis of dinucleoside tetraphosphate into constituent nucleoside diphosphates. A pyrophosphohydrolase has an activity as described in Plateau, P., et al., (1985) *Biochemistry* 24, 914-922.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

DESCRIPTION OF THE SPECIFIC EMBODIMENTS

A method for sequencing a nucleic acid is provided. In certain embodiments, the method includes contacting a nucleic acid duplex comprising a nucleic acid template and a primer annealed to the template with a reagent mix under primer extension conditions to produce an extended primer and ATP. The reagent mix may contain an adenosine-2'-deoxynucleoside tetraphosphate moiety and a polymerase. The method further includes detecting the produced ATP. Also provided are adenosine-2'-deoxynucleoside tetraphosphate moieties that find use in the subject methods. Also provided are kits containing the adenosine-2'-deoxynucleoside tetraphosphate moieties for use in the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Adenosine-2'-deoxynucleoside tetraphosphate compounds will be described first, followed by a detailed description of how the subject adenosine-2'-deoxynucleoside tetraphosphate compounds may be used to sequence a nucleic acid.

ADENOSINE-2'-DEOXYNUCLEOSIDE TETRAPHOSPHATE COMPOUNDS

Figure 1:
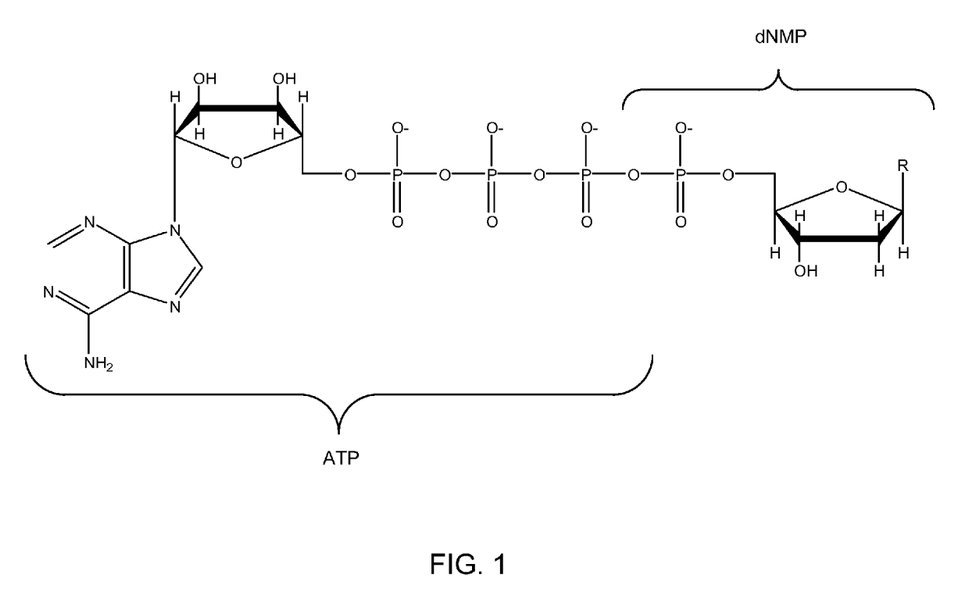
FIG. 1 shows the chemical structure of adenosine-2'-deoxynucleoside tetraphosphate.

Adenosine-2'-deoxynucleoside tetraphosphate (Ap₄dN) compounds that may be employed herein have the following formula:

wherein R is a 2'-deoxynucleoside.

As shown with reference to formula (I), the subject Ap₄dN compounds contain an adenosine substituent linked via four phosphate groups to a 2'-deoxynucleoside substituent through the 5'-hydroxyl of the 2'-deoxynucleoside substituent. In certain embodiments, the nucleoside base is adenine (A), thymine (T), guanine (G), cytosine (C), or an analog thereof, where an analog has a modified base retains an ability to base pair with a complementary nucleotide. In certain embodiments, the 2'-deoxynucleoside substituent is deoxyadenosine, deoxyguanosine, deoxycytidine, or thymidine. Stated alternatively, with reference to FIG. 1, the subject Ap₄dN compounds contain an adenosine triphosphate (ATP) substituent and a 2'-deoxynucleotide monophosphate (dNMP) substituent. In certain embodiments, the dNMP portion of the molecule is deoxyadenosine monophosphate (dAMP), deoxyguanosine monophosphate (dGMP), deoxycytidine monophosphate (dCMP), or thymidine monophosphate (TMP). The structures of exemplary Ap₄dN compounds are shown as follows: adenosine-2'-deoxyadenosine tetraphosphate (formula (II)); adenosine-2'-deoxycytidine tetraphosphate (formula (III)); adenosine-2'-deoxyguanosine tetraphosphate (formula (IV)); and adenosine-thymidine tetraphosphate (formula (V)).

-continued (V)

The subject compounds may be made enzymatically (e.g. using E. coli lysyl-tRNA synthetase as described in Plateau, P., et al., (1985) Biochemistry 24, 914-922) or using synthetic methods. Synthetic methods for making Ap$_4$dNs may include phosphitylation of a protected nucleoside with 2-chloro-4H-1,3,2-benzo-dioxaphosphorin-4-one (salicylchlorophosphite), followed by sequential reaction with inorganic pyrophosphate and a nucleoside 5'-monophosphate. Exemplary synthetic methods for making Ap$_4$dNs are described in Han, Q., et al., (2006) Organic Letters, 8(10), 2075-2077, as well as Reiss, J. R., and Moffatt, J. G., (1965) Journal Organic Chemistry, 30, 3381-3387; Feldhaus, P., et al., (1975) European Journal Biochemistry, 57, 197-204; and Shimazu, M., et al., (1990) Tetrahedron Letters, 31, 235-238, which publications are incorporated by reference for their disclosure of these methods.

As will be described in greater detail below, and with reference to FIG. 2, utilization of a subject Ap$_4$dN as a substrate for a template dependent polymerization reaction results in the incorporation of the dNMP substituent into the elongating primer, and the corresponding release of the ATP portion of Ap$_4$dN.

Also as will be described in greater detail below, the adenosine-2'-deoxynucleoside tetraphosphate compounds may be used in the sequencing methods described herein.

Methods

Methods for sequencing by synthesis are provided. In certain embodiments, and with reference to FIG. 2, the subject method includes contacting a nucleic acid duplex (i.e., a nucleic acid template with a primer annealed to the nucleic acid template) with a subject adenosine-2'-deoxynucleoside tetraphosphate (Ap$_4$dN) moiety and a polymerase under primer extension conditions to produce an extended primer and adenosine triphosphate (ATP). The method further includes detecting the produced ATP.

Figure 2:
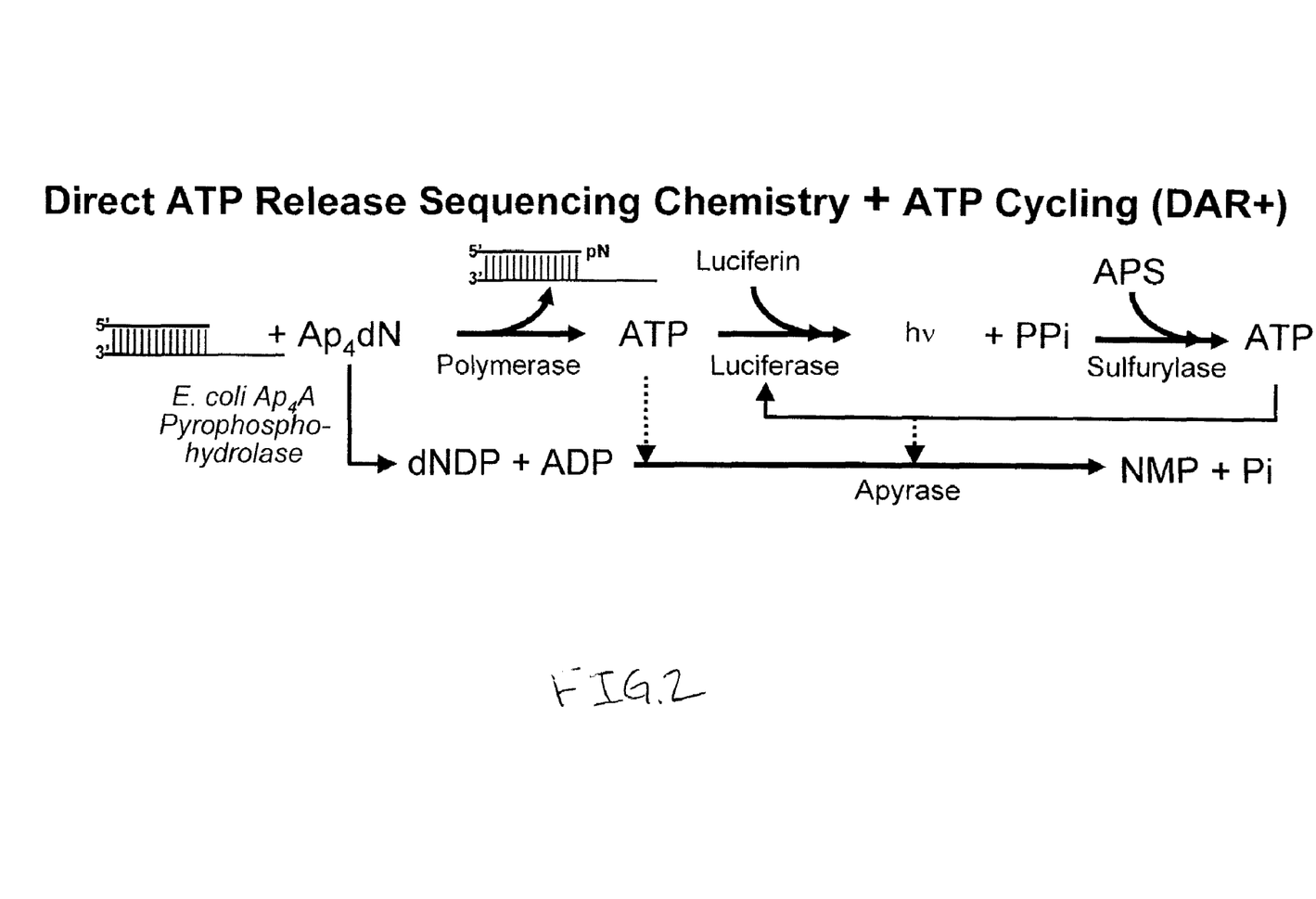
FIG. 2 shows a schematic illustration of direct ATP release sequencing chemistry.

In certain embodiments, and with reference to FIG. 2, a nucleic acid duplex comprising a primer annealed to the nucleic acid template is contacted with a reagent mix under primer extension conditions. In certain embodiments, the reagent mix includes an Ap$_4$dN moiety and a polymerase. If the Ap$_4$dN contains a dNMP substituent that is complementary to the next available base in the nucleic acid template, the polymerase incorporates the dNMP substituent of the Ap$_4$dN into the primer, thereby extending the length of the primer by one nucleotide. In addition, the polymerase correspondingly releases the ATP portion of the Ap$_4$dN. Thus, the amount of ATP released by the polymerase is proportional to the number of dNMPs incorporated into the elongating primer. The number of dNMPs incorporated into the elongating primer can be derived from the amount of light produced in the subsequent luciferin-luciferase reaction, as described below.

The ATP produced by the polymerase reaction can be detected in any of a variety of different ways. In certain embodiments, the ATP produced by the polymerase reaction is detected directly through a light-emitting enzymatic reaction. In certain embodiments, the ATP produced from the polymerase reaction is contacted with luciferin and an ATP-dependent luciferase enzyme. In certain embodiments, the luciferase is a surface-bound enzyme. In certain embodiments, the polymerase and the luciferase are incorporated into a single chimeric enzyme.

The ATP produced by the polymerase reaction is consumed in the luciferin-luciferase reaction, resulting in the production of inorganic pyrophosphate (PPi) and light (hυ). Thus, the amount of light produced is proportional to the amount of ATP released by the polymerase, which in turn is proportional to the number of dNMPs incorporated into the elongating primer. For example, if the nucleic acid template contains two consecutive identical nucleotides, and the Ap$_4$dN that contains the complementary nucleotide is added to the polymerase reaction, then two complementary nucleotides will be added to the elongating primer. Consequently, twice as much ATP will be released by the polymerase reaction, resulting in twice as much light being generated by the luciferin-luciferase reaction.

Importantly, in certain embodiments the present methods do not depend upon the release of PPi to initiate a cascade of reactions to produce a detectable light signal. Instead, as discussed above, the ATP necessary to initiate the light-emitting luciferin-luciferase reaction is released directly from the polymerase reaction.

In certain embodiments, the light generated by the luciferin-luciferase reaction is detected. Such detection methods are well-known and commonly employed in other sequencing methods, for example as in U.S. Pat. No. 6,613,523.

In certain embodiments, the subject method is repeated in series or in parallel using different Ap$_4$dNs. For example, the method can be performed in series, first with adenosine-2'-deoxyadenosine tetraphosphate (Ap$_4$dA), then with adenosine-2'-deoxyguanosine tetraphosphate (Ap$_4$dG), then with adenosine-2'-deoxycytidine tetraphosphate (Ap$_4$dC), and finally with adenosine-thymidine tetraphosphate (Ap$_4$T). The generation of light from one of these reactions indicates which corresponding dNMP has been added to the elongating primer, and consequently indicates what the complementary base is in the sequence of the nucleic acid template. Thus, multiple iterations of the subject method using different Ap$_4$dNs can be used to determine the sequence of the nucleic acid template.

In certain embodiments, the subject method is performed in parallel reactions, with each reaction using a different $Ap_4dN$. In certain embodiments, the subject method is performed in a series of parallel reactions, with each reaction within a series using a different $Ap_4dN$.

Also provided is a method of sequencing a nucleic acid comprising: (a) sequentially contacting a nucleic acid duplex comprising a nucleic acid template and a primer annealed to said nucleic acid template with, in any order: (i) adenosine-2'-deoxycytidine tetraphosphate; (ii) adenosine-2'-deoxyguanosine tetraphosphate; (iii) adenosine-2'-deoxyadenosine tetraphosphate; and (iv) adenosine-thymidine tetraphosphate; and a polymerase under primer extension conditions; and (b) detecting which of said reactions produces ATP, wherein ATP production indicates the nucleotide added to said primer.

In certain embodiments, many hundreds or many thousands or millions of nucleic acid templates may be sequenced in parallel in spatially addressable reactions, e.g. distributed on a 96-well plate, beads or array. In certain embodiments, all the spatially addressable reactions receive the same chemistry in parallel, e.g. through use of a flow cell.

In certain embodiments, and with reference to FIG. 2, the PPi produced by the luciferin-luciferase reaction is contacted with adenosine 5'-phosphosulfate (APS) and an ATP sulfurylase. In certain embodiments, the sulfurylase is a surface-bound enzyme. In certain embodiments, the sulfurylase and luciferase enzymes are immobilized on the same solid support. In certain embodiments, the luciferase and sulfurylase are incorporated into a single chimeric enzyme. The PPi produced by the luciferin-luciferase reaction is regenerated into ATP by sulfurylase. The resulting ATP can be cycled through the luciferin-luciferase reaction to increase the overall signal and improve the sensitivity of the method.

In certain embodiments, and with reference to FIG. 2, the reagent mix includes an enzyme that degrades $Ap_4dNs$. In certain embodiments, the enzyme is a pyrophosphohydrolase. In certain embodiments, the enzyme is E. coli pyrophosphohydrolase. The pyrophosphohydrolase hydrolyzes $Ap_4dNs$ into 2'-deoxynucleotide diphosphate (dNDP) moieties and adenosine diphosphate (ADP).

In certain embodiments, and with reference to FIG. 2, the reagent mix includes a nucleotide degrading enzyme. In certain embodiments, the nucleotide degrading enzyme is apyrase. In certain embodiments, the apyrase is a surface-bound enzyme. Apyrase converts residual ATP, APS, ADP, and dNDPs to nucleotide monophosphates (NMPs) and inorganic monophosphate (Pi). Removal of residual ATP, APS, ADP, and dNDPs eliminates their potential interference with the desired reaction pathway. In certain embodiments, the apyrase is contacted with the reaction mixture after light has been detected. In certain embodiments, the apyrase is removed prior to a subsequent iteration of the subject method.

In certain embodiments, a method of sequencing a nucleic acid is provided. The method includes, in a plurality of reactions, separately contacting a nucleic acid duplex comprising a primer annealed to a nucleic acid template with: (i) adenosine-2'-deoxycytidine tetraphosphate; (ii) adenosine-2'-deoxyguanosine tetraphosphate; (iii) adenosine-2'-deoxyadenosine tetraphosphate; or (iv) adenosine-thymidine tetraphosphate; and a polymerase under primer extension conditions. The method further includes detecting which of the plurality of reactions produces ATP. By detecting which reaction produces ATP, the identity of the nucleotide added to the elongating primer can be determined because, as described above, ATP is only released if a nucleotide is added to the elongating primer. Consequently, this indicates the identity of the corresponding complementary nucleotide of the nucleic acid template.

In certain embodiments, and as described above, the present method is repeated. Thus, the sequence of the nucleic acid template can be determined.

In certain embodiments, and as described above, the ATP produced by the polymerase reaction can be detected directly through an enzymatic reaction. In certain embodiments, the ATP produced from the polymerase reaction is contacted with luciferin and an ATP-dependent luciferase enzyme. In certain embodiments, the luciferase is a surface-bound enzyme. The ATP produced by the polymerase reaction is consumed in the luciferin-luciferase reaction, resulting in the production of inorganic pyrophosphate (PPi) and light (hυ). Thus, in certain embodiments the present methods do not depend upon the release of PPi to produce a detectable light signal. Instead, as discussed above, the ATP necessary to initiate the light-emitting luciferin-luciferase reaction is released directly from the polymerase reaction.

Any polymerase capable of catalyzing a template-dependent addition of a nucleotide to a primer may be employed in the instant methods. Depending on the characteristics of the target nucleic acid, a DNA polymerase, an RNA polymerase, a reverse transcriptase, or a mutant or altered form of any of the foregoing can be used.

DNA polymerases useful in the invention include, but are not limited to: Pyrococcus furiosus (Pfu) DNA polymerase (Lundberg et al., 1991, Gene, 108: 1, Stratagene), Pyrococcus woesei (Pwo) DNA polymerase (Hinnisdaels et al., 1996, Biotechniques, 20:186-8, Boehringer Mannheim), Thermus thermophilus (Tth) DNA polymerase (Myers and Gelfand 1991, Biochemistry 30:7661), Bacillus stearothermophilus DNA polymerase (Stenesh and McGowan, 1977, Biochim Biophys Acta 475:32), Thermococcus litoralis (Tli) DNA polymerase (also referred to as Vent™ DNA polymerase, Cariello et al., 1991, Polynucleotides Res, 19: 4193, New England Biolabs), Stoffel fragment, ThermoSequenase™ (Amersham Pharmacia Biotech UK), Terminator™ (New England Biolabs), Thermotoga maritima (Tma) DNA polymerase (Diaz and Sabino, 1998 Braz J. Med. Res, 31:1239), Thermus aquaticus (Taq) DNA polymerase (Chien et al., 1976, J. Bacteoriol, 127: 1550), Pyrococcus kodakaraensis KOD DNA polymerase (Takagi et al., 1997, Appl. Environ. Microbiol. 63:4504), JDF-3 DNA polymerase (from thermococcus sp. JDF-3, Patent application WO 0132887), Pyrococcus GB-D (PGB-D) DNA polymerase (also referred as Deep Vent™ DNA polymerase (Juncosa-Ginesta et al., 1994, Biotechniques, 16:820, New England Biolabs), UlTma DNA polymerase (from thermophile Thermotoga maritima; Diaz and Sabino, 1998 Braz J. Med. Res, 31:1239; PE Applied Biosystems), Tgo DNA polymerase (from Thermococcus gorgonarius, Roche Molecular Biochemicals), E. coli DNA polymerase I (Lecomte and Doubleday, 1983, Polynucleotides Res. 11:7505), T7 DNA polymerase (Nordstrom et al., 1981, J. Biol. Chem. 256:3112), and archaeal DP1I/DP2 DNA polymerase II (Cann et al., 1998, Proc Natl Acad. Sci. USA 95:14250).

In particular cases, the polymerase may be a polymerase that has been selected specifically because it has high affinity for the above-described substrates. In certain embodiments, the Michaelis-Menten constant ($K_m$) of the $Ap_4dN$ for the polymerase is comparable to the $K_m$ of natural dNTPs (i.e., less than about 20 μM).

In certain embodiments, a polymerase may be subjected to so-called "directed evolution" methods that select for a polymerase with altered affinity for $Ap_4dN$. A variety of such directed evolution methods are known in the art, including but not limited to DNA shuffling (PCT WO 00/42561 A3; PCT WO 01/70947 A3), exon shuffling (U.S. Pat. No. 6,365,377;

Kolkman & Stemmer, 2001, Nat Biotechnol 19:423-428), family shuffling (Crameri et al., 1998, Nature 391:288-291; U.S. Pat. No. 6,376,246), RACHITT™ (Coco et al., 2001, Nat Biotechnol 19:354-359; PCT WO 02/06469), STEP and random priming of in vitro recombination (Zhao et al., 1998, Nat Biotechnol 16:258-261; Shao et al., 1998, Nucleic Acids Res 26:681-683), exonuclease mediated gene assembly (U.S. Pat. No. 6,352,842; U.S. Pat. No. 6,361,974), Gene Site Saturation Mutagenesis™ (U.S. Pat. No. 6,358,709), Gene Reassembly™ (U.S. Pat. No. 6,358,709), SCRATCHY (Lutz et al., 2001, Proc Natl Acad Sci USA 98:11248-11253), DNA fragmentation methods (Kikuchi et al., Gene 236:159-167), single-stranded DNA shuffling (Kikuchi et al., 2000, Gene 243:133-137), and AMEsystem™ directed evolution protein engineering technology (Applied Molecular Evolution) (U.S. Pat. No. 5,824,514; U.S. Pat. No. 5,817,483; U.S. Pat. No. 5,814,476; U.S. Pat. No. 5,763,192; U.S. Pat. No. 5,723,323).

Kits

Kits for use in practicing certain methods described herein are also provided. In certain embodiments, the kits include at least four different adenosine-2'-deoxynucleoside tetraphosphates, e.g., adenosine-2'-deoxycytidine tetraphosphate, adenosine-2'-deoxyguanosine tetraphosphate, adenosine-2'-deoxyadenosine tetraphosphate, and adenosine-thymidine tetraphosphate. A kit may further include a polymerase. A kit may further include reagents for detecting ATP, including, but not limited to: a luciferase and luciferin. In certain cases, a kit may further contain adenosine 5'-phosphosulfate, an ATP sulfurylase, an apyrase, a pyrophosphohydrolase, etc. A kit may further include additional reagents employed in the methods of the invention, e.g., buffers, oxidizing agents, capping agents, cleavage agents, etc. In certain embodiments, the kits will further include instructions for practicing the subject methods or means for obtaining the same (e.g., a website URL directing the user to a webpage which provides the instructions), where these instructions may be printed on a substrate, where substrate may be one or more of: a package insert, the packaging, reagent containers and the like. In the subject kits, the one or more components are present in the same or different containers, as may be convenient or desirable.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method comprising:
    (a) contacting a nucleic acid duplex comprising a nucleic acid template and a primer annealed to said nucleic acid template with a reagent mix comprising an adenosine-2'-deoxynucleoside tetraphosphate moiety and a polymerase under primer extension conditions to produce an extended primer and adenosine triphosphate (ATP); and
    (b) detecting said ATP.

2. The method of claim 1, wherein said adenosine-2'-deoxynucleoside tetraphosphate moiety has the following formula:

wherein R is a 2'-deoxynucleoside.

3. The method of claim 2, wherein R is 2'-deoxyadenosine, 2'-deoxycytidine, 2'-deoxyguanosine, or thymidine.

4. The method of claim 1, wherein said contacting results in the incorporation of a nucleotide into said extended primer that is complementary to the corresponding nucleotide of said nucleic acid template.

5. The method of claim 4, further comprising repeating steps (a) and (b) using different adenosine-2'-deoxynucleoside tetraphosphate moieties, thereby determining the sequence of said nucleic acid template.

6. The method of claim 1, wherein said detecting comprises contacting said ATP with luciferin and an ATP-dependent luciferase enzyme to produce pyrophosphate (PPi) and light.

7. The method of claim 6, wherein the amount of light produced is proportional to the amount of said ATP produced.

8. The method of claim 6, wherein said reagent mix further comprises adenosine 5'-phosphosulfate (APS) and sulfurylase, and wherein said method further comprises contacting said produced PPi and said APS with said sulfurylase to produce ATP.

9. The method of claim 1, wherein said reagent mix further comprises an enzyme that degrades said adenosine-2'-deoxynucleoside tetraphosphate moiety.

10. The method of claim 9, wherein said enzyme is a pyrophosphohydrolase.

11. The method of claim 1, further comprising:
    (c) contacting said reagent mix with a nucleotide degrading enzyme.

12. The method of claim 11, wherein said nucleotide degrading enzyme is apyrase.

13. The method of claim 11, wherein said nucleotide degrading enzyme is added after said detecting, and then removed prior to a subsequent primer extension.

14. A method of sequencing a nucleic acid comprising:
    (a) separately contacting a nucleic acid duplex comprising a nucleic acid template and a primer annealed to said nucleic acid template with:
        (i) adenosine-2'-deoxycytidine tetraphosphate;
        (ii) adenosine-2'-deoxyguanosine tetraphosphate;
        (iii) adenosine-2'-deoxyadenosine tetraphosphate; or
        (iv) adenosine-thymidine tetraphosphate; and
    a polymerase under primer extension conditions to produce a plurality of reactions;
    (b) detecting which of said reactions produces ATP, wherein ATP production indicates the nucleotide added to said primer.

15. The method of claim 14, wherein said separately contacting results in the incorporation of a nucleotide into said extended primer that is complementary to the corresponding nucleotide of said nucleic acid template.

16. The method of claim 15, further comprising repeating steps (a) and (b), thereby determining the sequence of said nucleic acid template.

17. The method of claim 14, wherein said detecting comprises reacting said ATP with luciferin and an ATP-dependent luciferase enzyme to produce pyrophosphate (PPi) and light.

18. A method of sequencing a nucleic acid comprising:
(a) sequentially contacting a nucleic acid duplex comprising a nucleic acid template and a primer annealed to said nucleic acid template with, in any order:
  (i) adenosine-2'-deoxycytidine tetraphosphate;
  (ii) adenosine-2'-deoxyguanosine tetraphosphate;
  (iii) adenosine-2'-deoxyadenosine tetraphosphate; and
  (iv) adenosine-thymidine tetraphosphate; and
a polymerase under primer extension conditions; and
(b) detecting which of said reactions produces ATP, wherein ATP production indicates the nucleotide added to said primer.

19. A kit comprising:
(i) adenosine-2'-deoxycytidine tetraphosphate;
(ii) adenosine-2'-deoxyguanosine tetraphosphate;
(iii) adenosine-2'-deoxyadenosine tetraphosphate;
(iv) adenosine-thymidine tetraphosphate; and
(v) a polymerase.

20. The kit of claim 18, further comprising compounds selected from the group consisting of: luciferin and a luciferase; adenosine 5'phosphosulfate and a sulfurylase; an apyrase; and a pyrophosphohydrolase.

* * * * *